(12) United States Patent
Huang et al.

(10) Patent No.: US 10,485,836 B2
(45) Date of Patent: Nov. 26, 2019

(54) ANTI-FATIGUE COMPOSITION USED FOR INCREASING ENDURANCE PERFORMANCE, AND USE OF THE SAME

(71) Applicant: SINPHAR PHARMACEUTICAL CO., LTD., Dongshan Township, Yilan County (TW)

(72) Inventors: Wen-Pang Huang, Dongshan Township, Yilan County (TW); Ya-Ting Wu, Dongshan Township, Yilan County (TW)

(73) Assignee: SINPHAR PHARMACEUTICAL CO., LTD., Dongshan Township, Yilan County (TW)

( * ) Notice: Subject to any disclaimer, the term of this patent is extended or adjusted under 35 U.S.C. 154(b) by 0 days.

(21) Appl. No.: 15/895,010

(22) Filed: Feb. 13, 2018

(65) Prior Publication Data
US 2018/0243360 A1  Aug. 30, 2018

Related U.S. Application Data (60) Provisional application No. 62/458,304, filed on Feb. 13, 2017.

(51) Int. Cl.
| | | |
|---|---|---|
| *A61K 36/64* | (2006.01) | |
| *A61K 31/122* | (2006.01) | |
| *A61K 31/09* | (2006.01) | |
| *A61K 9/00* | (2006.01) | |
| *A23L 33/105* | (2016.01) | |
| *A61K 45/06* | (2006.01) | |

(52) U.S. Cl.
CPC ............ *A61K 36/64* (2013.01); *A23L 33/105* (2016.08); *A61K 9/0019* (2013.01); *A61K 31/09* (2013.01); *A61K 31/122* (2013.01); *A61K 45/06* (2013.01); *A23V 2002/00* (2013.01); *A23V 2200/326* (2013.01); *A23V 2250/21* (2013.01); *A23V 2250/314* (2013.01)

(58) Field of Classification Search
None
See application file for complete search history.

(56) References Cited

U.S. PATENT DOCUMENTS

2010/0061969 A1* 3/2010 Otsubo .................. A21D 2/14
424/94.1

FOREIGN PATENT DOCUMENTS

| CN | 104605348 A | * | 5/2015 |
| CN | 105233274 | | 1/2016 |
| JP | 2012067023 | | 4/2012 |

OTHER PUBLICATIONS

International Search Report and Written Opinion of International Application No. PCT/CN2018/076630, dated May 2018.
Tu, P. et al., "Cistanche research and its industrial development", Chin. Pharm J., 2011, vol. 46(12).
The full text of the Food Composition Table of the Premium QH Capsule, Oct. 16, 2015.
The full text of the Marka Enzyme Liquid Composition Table, Nov. 11, 2013.

* cited by examiner

*Primary Examiner* — Susan Hoffman
(74) *Attorney, Agent, or Firm* — Ping Wang; Morris, Manning, & Martin, LLP (57) ABSTRACT

A composition and its use in anti-fatigue are provided, wherein the composition comprises a first component being a *Cistanche tubulosa* extract and a second component being ubiquinone (Q10) and/or ubiquinol (QH), and the weight ratio of the first component to the second component ranges from 0.67:1 to 10:1. The composition is used for anti-fatigue and is a pharmaceutical composition, a food composition, a cosmetic composition, a care product composition, or a feed composition. The pharmaceutical composition is used for treating or preventing chronic fatigue syndrome, and the food composition, the cosmetic composition, the care product composition and the feed composition are used for at least one of increasing endurance performance, increasing athletic ability, increasing physical strength, recovering physical strength, promoting fatigue elimination, preventing myocardial weakness, helping ameliorate myocardial weakness and helping improve cardiac function.

6 Claims, 6 Drawing Sheets

ANTI-FATIGUE COMPOSITION USED FOR INCREASING ENDURANCE PERFORMANCE, AND USE OF THE SAME

FIELD OF THE INVENTION

The present invention relates to a composition, which comprises a first component being a *Cistanche tubulosa* extract and a second component being ubiquinone (Q10) and/or ubiquinol (QH). The present invention also relates to the uses of the composition in anti-fatigue, especially relates to the uses of the composition in at least one of treating chronic fatigue syndrome, preventing chronic fatigue syndrome, increasing endurance performance, increasing athletic ability, increasing physical strength, recovering physical strength, promoting fatigue elimination, preventing myocardial weakness, helping ameliorate cardiac weakness, and helping improve cardiac function. In the aforementioned composition, the weight ratio of the first component to the second component ranges from 0.67:1 to 10:1.

BACKGROUND OF THE INVENTION

The term "fatigue" refers to the incapability of a body to keep its' physiological functions working at a certain level and/or the incapability of organs (e.g., heart) to keep their original working abilities, and thus, result in decreased athletic ability and decreased physical strength. However, exposure to excessive stresses or excessive works for a long time may inhibit the body from getting adequate rest, and thus, cannot eliminate the feeling of fatigue or tiredness. The feeling of fatigue or tiredness is a warning of the body, and such feeling can be eliminated by getting rest in general. However, exposure to a condition of excessive stresses or excessive works for a long time may inhibit the body from getting adequate rest, and thus, may cause a severe feeling of body fatigue, occurrence of chronic fatigue syndrome (CFS) such as swollen lymph nodes, slight fever, headache, muscle soreness, joint aches, decreased thinking ability, reduced concentration, and somnipathy. When serious, it may result in myocardial weakness and decreased cardiac function, and even may cause an accident and endanger one's life. Therefore, there is a necessity for continuously developing an effective method or drug for anti-fatigue to reduce the social costs for the injuries and diseases caused by fatigue.

Herba *Cistanche* was firstly recorded in "Shennong Bencaojing" and is a perennial parasitic herb belonging to the genus *Cistanche* and the family Orobanchaceae. Herba *Cistanche*, which is supported by absorbing the nutrients from the host plant, Red willow (*Tamarix ramosissima*) and distributed in dry areas such as deserts and barrens, is a valuable and rare herb. Ubiquinone (Q10), which primarily presents in the mitochondria of eukaryotes and acts as a coenzyme in the electron transport chain and thus participates in the aerobic respiration of cells, can promote the production of ATP to supply energy to cells. Ubiquinol (QH), which is a reduced form of ubiquinone (Q10), can be directly absorbed and utilized by human body without a conversion, and thus, has a higher bioavailability than that of ubiquinone (Q10).

Inventors of the present invention found a composition that is capable of providing an excellent effect on anti-fatigue, comprising a first component being a *Cistanche tubulosa* extract and a second component being ubiquinone (Q10) and/or ubiquinol (QH), wherein the weight ratio of the first component to the second component ranges from 0.67:1 to 10:1, and the composition can be used for at least one of treating chronic fatigue syndrome, preventing chronic fatigue syndrome, increasing endurance performance, increasing athletic ability, increasing physical strength, recovering physical strength, promoting fatigue elimination, preventing myocardial weakness, helping ameliorate cardiac weakness, and helping improve cardiac function. By using a combination of the aforementioned first component and second component, the present invention provides a composition with excellent effects on anti-fatigue under relative low manufacturing costs, and thus, has high economic benefits.

SUMMARY OF THE INVENTION

An objective of the present invention is to provide a composition, comprising a first component being a *Cistanche tubulosa* extract and a second component being ubiquinone (Q10) and/or ubiquinol (QH), wherein the weight ratio of the first component to the second component ranges from 0.67:1 to 10:1. Preferably, the *Cistanche tubulosa* extract is a polar solvent extract of *Cistanche tubulosa*, wherein the polar solvent is selected from a group consisting of water, C1-C4 alcohols, and combinations thereof.

Preferably, the composition provided in accordance with the present invention further comprises at least one of vitamin B complex, a *Rhodiola rosea* extract, a *Schisandra chinensis* extract, vitamin E, ribose, a hawthorn (*Crataegus* spp.) extract, magnesium, calcium, fish oil, taurine, chicken essence, an *Acanthopanax senticosus* extract, a *Panax ginseng* extract, clam essence, a *Cordyceps sinensis* extract, a soybean protein isolate, a branched-chain amino acid (BCAA), carnitine, isomaltulose, glucose, a probiotic, a whey protein, a milk protein isolate, gamma aminobutyric acid (GABA), a *gastrodia elata* extract, L-tryptophan, and γ-oryzanol. More preferably, the composition further comprises one selected from a group consisting of vitamin B1, a derivative of vitamin B1, vitamin B6, a derivative of vitamin B6, and combinations thereof.

Preferably, the composition provided in accordance with the present invention is used for anti-fatigue and is a pharmaceutical composition, a food composition, a cosmetic composition, a care product composition, or a feed composition. In one embodiment of the pharmaceutical composition provided in accordance with the present invention, the pharmaceutical composition is used for treating chronic fatigue syndrome or preventing chronic fatigue syndrome. Preferably, the pharmaceutical composition is in a dosage form for oral administration, transdermal administration, intravenous injection or subcutaneous injection.

Preferably, the food composition, cosmetic composition, care product composition or feed composition provided in accordance with the present invention is used for anti-fatigue and for at least one of increasing endurance performance, increasing athletic ability, increasing physical strength, recovering physical strength, promoting fatigue elimination, preventing myocardial weakness, helping ameliorate cardiac weakness, and helping improve cardiac function. The food composition could be a health food, a dietary supplement, a functional food, a nutritional supplement food, or a special nutritional food. Preferably, the food composition is a milk product, a processed meat product, breadstuff, pasta, cookies, a troche, a capsule, a fruit juice, a tea product, a sport beverage, a nutritional beverage, a soup juice, powder, a jelly, a soft candy, a solid-liquid mixed soup product, or a solid-liquid mixed beverage.

Another objective of the present invention is to provide a method for anti-fatigue, comprising administering to a subject in need an effective amount of the above composition. The method of the present invention can be for at least one of treating chronic fatigue syndrome, preventing chronic fatigue syndrome, increasing endurance performance, increasing athletic ability, increasing physical strength, recovering physical strength, promoting fatigue elimination, preventing myocardial weakness, helping ameliorate cardiac weakness, and helping improve cardiac function.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 3 shows the time to exhaustion of weight-bearing swimming mice, including the results of "Vehicle group", "Group I", "Group II" and "Group III", wherein "Vehicle group" was fed with a composition containing only a vehicle (i.e., a composition free of *Cistanche tubulosa* extract and ubiquinol); "Group I" was fed with a composition containing a vehicle and a mixture of *Cistanche tubulosa* extract and ubiquinol at a weight ratio of *Cistanche tubulosa* extract:ubiquinol=1.67:1; "Group II" was fed with a composition containing a vehicle and a mixture of *Cistanche tubulosa* extract and ubiquinol at a weight ratio of *Cistanche tubulosa* extract:ubiquinol=3.33:1; and "Group III" was fed with a composition containing a vehicle and a mixture of *Cistanche tubulosa* extract and ubiquinol at a weight ratio of *Cistanche tubulosa* extract:ubiquinol=6.67:1.

FIGS. 5A to 5E show the serum biochemical values of the above "Vehicle group", "Group I", "Group II" and "Group III" in mice after swimming exercise, wherein

DESCRIPTION OF THE PREFERRED EMBODIMENTS

The detailed technology and preferred embodiments implemented for the present invention are described in the following paragraphs for people skilled in this field to well appreciate the features of the claimed invention. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms. The term "an effective amount" used in this specification refers to the dosage of the composition that can at least partially reduce the feelings of fatigue and tiredness in a subject or alleviate the symptoms of chronic fatigue syndrome of a subject when administered to the subject. The term "subject" used in this specification refers to a mammalian, including human and non-human animals. The term "prevent" or "preventing" recited in this specification refers to inhibiting or preventing a particular condition of illness from breaking out, or maintaining good health in a sensitive subject to tolerate diseases. The term "treat" or "treating" recited in this specification should not be construed as treating a subject until the subject is completely recovered but should include maintaining the progression or symptoms of the diseases in a substantially static state, increasing the recovery rate of a subject, alleviating the severity of a particular condition of illness, or increasing the quality of life of a patient.

In this specification, the "weight ratio" among the components in the composition is calculated on a dry basis, i.e., the weight ratio is calculated based on the dry weight of each component (e.g., the dry weight each of the first component and the second component). The phrase "endurance performance" refers to the length of time in which muscles can continuously perform in the presence of resistance.

The numerical ranges (e.g., 5 to 100) used in this specification should be construed as including all of the rational numbers in the ranges and ranges consisting of any rational numbers in the ranges. Therefore, the numerical ranges used in this specification should include all the possible combinations of numerical values between the lowest value and the highest value listed therein. In addition, the word "about" as used herein substantially represents values within ±10% of the stated value, preferably within ±5%.

As described above, exposure to the condition of fatigue for a long episode may cause occurrence of chronic fatigue syndrome. When serious, it may result in myocardial weakness and decreased cardiac function. Inventors of the present invention found that a composition comprising a first component being a *Cistanche tubulosa* extract and a second component being ubiquinone (Q10) and/or ubiquinol (QH), particularly a composition comprising the aforementioned first component and second component at a weight ratio ranging from 0.67:1 to 10:1, can effectively alleviate the TNF-α induced decrease in oxygen consumption rate of cells, alleviate the TNF-α induced abnormal in extracellular acidification rate, increase the endurance and the muscle strength performances of mice, reduce the metabolites in the blood of mice after exercise, provide the reserved energy in the blood of mice, and thus, is effective in anti-fatigue. It is believed that the above composition can be used for at least one of treating chronic fatigue syndrome, preventing chronic fatigue syndrome, increasing endurance performance, increasing athletic ability, increasing physical strength, recovering physical strength, promoting fatigue elimination, preventing myocardial weakness, helping ameliorate cardiac weakness, and helping improve cardiac function. Therefore, the present invention provides a composition comprising a first component being a *Cistanche tubulosa* extract and a second component being ubiquinone (Q10) and/or ubiquinol (QH), wherein the weight ratio of the first component to the second component ranges from 0.67:1 to 10:1, preferably from 0.67:1 to 6.67:1, and more preferably from 1.67:1 to 6.67:1.

In the composition according to the present invention, the *Cistanche tubulosa* extract could be a liquid extract or a dry matter provided by drying the liquid extract, wherein, the liquid extract is provided by extracting *Cistanche tubulosa* material with a polar solvent. The *Cistanche tubulosa* material could be any part of *Cistanche tubulosa*, for example, the stem, flower, or whole plant of *Cistanche tubulosa* could be used as an extraction material. In one embodiment according to the present invention, the succulent stem of *Cistanche tubulosa* is used as the extraction material. The polar solvent that is adopted could be water, C1-C4 alcohols, or combinations thereof. Preferably, the polar solvent could be water, ethanol, or a combination thereof. The amount ratio of the polar solvent for extraction and *Cistanche tubulosa* material could be optionally adjusted. In general, there is no particular limitation of the amount of polar solvent, as long as the materials can be dispersed in the polar solvent evenly. To achieve as high of an extraction efficiency as possible, the extraction of the *Cistanche tubulosa* material could be optionally repeated with the same or different polar solvent, and the liquid extracts thus obtained from multiple times extractions could be combined and subjected to desiccation.

In the above extraction step, the extraction time could be optionally adjusted to achieve a desired extraction degree. For example, when using water as the extraction solvent, the extraction is usually conducted for at least 15 minutes, preferably at least 30 minutes, and more preferably at least 60 minutes. Furthermore, the extraction step could be optionally accompanied with other operations such as decoction, cooling, filtration, vacuum concentration, and resin column chromatography to enhance the extraction efficiency.

Ubiquinone (Q10) and/or ubiquinol (QH) as the second component comprised in the composition of the present invention could be provided by any suitable source. For example, ubiquinone and/or ubiquinol could be purchased commercially, provided by microbial fermentation, or obtained from chemical synthesis. For example, ubiquinone and ubiquinol could be purchased from Kaneka company.

The composition provided according to the present invention could optionally further comprise one or more other active ingredient(s), or be used in combination with a medicament or a food product comprising one or more other active ingredient(s), to further enhance the effects of the composition, or to increase the application flexibility and adaptability of the preparation thus provided, as long as the other active ingredients do not adversely affect the desired effects of the first component and the second component of the present invention. Examples of the other active ingredients include, but is not limited to, vitamin B complex, a *Rhodiola rosea* extract, a *Schisandra chinensis* extract, vitamin E, ribose, a hawthorn (*Crataegus* spp.) extract, magnesium, calcium, fish oil, taurine, chicken essence, an *Acanthopanax* senticosus extract, a *Panax ginseng* extract, clam essence, a *Cordyceps sinensis* extract, a soybean protein isolate, a branched-chain amino acid (BCAA), carnitine, isomaltulose, glucose, a probiotic, a whey protein, a milk protein isolate, gamma aminobutyric acid (GABA), a *gastrodia* data extract, L-tryptophan, and γ-oryzanol. Preferably, the composition of the present invention comprises one selected from a group consisting of vitamin B1, a derivative of vitamin B1, vitamin B6, a derivative of vitamin B6, and combinations thereof.

The composition provided according to the present invention could be a pharmaceutical composition, a food composition, a cosmetic composition, a care product composition or a feed composition. Depending on the desired purpose, the pharmaceutical composition could be provided in any suitable form without specific limitations. For example, the pharmaceutical composition could be administered to a subject in need by an oral or parenteral (such as transdermal, subcutaneous injection, and intravenous injection) route, but the administration is not limited thereby. Depending on the form and purpose, suitable carriers could be chosen and used to provide the pharmaceutical composition, wherein the carriers include excipients, diluents, auxiliaries, stabilizers, absorbent retarders, disintegrating agent, hydrotropic agents, emulsifiers, antioxidants, adhesives, binders, tackifiers, dispersants, suspending agents, lubricants, hygroscopic agents, etc.

As a dosage form for oral administration, the pharmaceutical composition provided according to the present invention could comprise any pharmaceutically acceptable carrier that will not adversely affect the desired effects of the first component and the second component of the present invention. For example, the pharmaceutically acceptable carrier could be water, saline, dextrose, glycerol, ethanol or its analogs, cellulose, starch, sugar bentonite, and combinations thereof. The pharmaceutical composition could be provided in any suitable form for oral administration, such as in a form of a tablet (e.g., sugar coated tablet), a pill, a capsule, granules, a pulvis, a fluidextract, a solution, a syrup, a suspension, a tincture.

As a dosage form for transdermal administration, the pharmaceutical composition provided according to the present invention could be in a form such as a patch, an emulsion, a cream, a gel (such as a hydrogel), a paste (such as a dispersing paste, an ointment), a spray, or a solution (such as a suspension) for external use, but is not limited thereby.

As for the form of injections or drips suitable for subcutaneous, intravenous administration, the pharmaceutical composition provided according to the present invention could comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the pharmaceutical composition as an intravenous infusion, an emulsified intravenous infusion, a powder for injection, a suspension for injection, or a powder suspension for injection, etc. Alternatively, the pharmaceutical composition could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the need, age, body weight, and health conditions of the subject, the pharmaceutical composition provided according to the present invention could be dosed with various administration frequencies, such as once a day, multiple times a day, once every few days, etc. The ratio of amount of the first component and the second component in the pharmaceutical composition provided according to the present invention could be adjusted depending on the requirements of practical application.

Optionally, the pharmaceutical composition, food composition, cosmetic composition, care product composition or feed composition provided according to the present invention could further comprise a suitable amount of additives, such as a flavoring agent, a toner, or a coloring agent for enhancing the palatability and the visual perception of the pharmaceutical composition, food composition, cosmetic composition, care product composition or feed composition, and/or a buffer, a conservative, a preservative, an antibacterial agent, or an antifungal agent for improving the stability and storability of the pharmaceutical composition, food composition, cosmetic composition, care product composition or feed composition.

The food composition provided according to the present invention could be a health food, a dietary supplement, a functional food, a nutritional supplement food, or a special nutritional food, and could be manufactured into such as a milk product, a processed meat product, breadstuff, pasta, cookies, a troche, a capsule, a fruit juice, a tea product, a sport beverage, a nutritional beverage, a soup juice, powder, a jelly, a soft candy, a solid-liquid mixed soup product, or a solid-liquid mixed beverage, but is not limited thereby.

Depending on the age, body weight and health conditions of the subject, the health food, dietary supplement, functional food, nutritional supplement food and special nutritional food provided according to the present invention could be taken with various frequencies, such as once a day, multiple times a day, once every few days, etc. The contents of the first component and the second component in the health food, dietary supplement, functional food, nutritional supplement food and special nutritional food provided according to the present invention could also be adjusted, and preferably could be adjusted to the amount that should be taken daily, depending on the specific population.

The recommended dosage, use standards and use conditions for a specific population (e.g., athletes, heart disease patients, diabetes mellitus patients, pregnant women, elders and sarcopenia patients), or the recommendations for a use in combination with other food products or pharmaceuticals could be indicated on the exterior package of the health food, dietary supplement, functional food, nutritional supplement food and/or special nutritional food provided according to the present invention. Thus, it is suitable for the user to take the health food, dietary supplement, functional food, nutritional supplement food and/or special nutritional food by him- or herself safely and securely without the instructions of a doctor, pharmacist, or related executive.

The cosmetic composition and care product composition provided according to the present invention can be used for at least one of increasing endurance performance, increasing athletic ability, increasing physical strength, recovering physical strength, promoting fatigue elimination, preventing myocardial weakness, helping ameliorate cardiac weakness, and helping improve cardiac function. The care product composition provided according to the present invention could be in any suitable form without specific limitations. For example, the care product composition could be in a form of an emulsion, a cream, a gel (such as a hydrogel), or a solution (such as an essence, a lotion) for external use, but is not limited thereby.

When administering the cosmetic composition or care product composition provided according to the present invention to increase endurance performance, increase athletic ability, increase physical strength, recover physical strength, promote fatigue elimination, prevent myocardial weakness, help ameliorate cardiac weakness, and/or help improve cardiac function, the contents of the first component and the second component could be various depending on the product type.

The feed composition provided according to the present invention could comprise any edible materials that will not adversely affect the desired effects of the first component and the second component of the present invention. For example, the edible materials could be an emulsifier, skim milk powders, a soybean protein, carbohydrates, starches, processes starches, dextrin, salts such as inorganic salts or organic salts. The feed composition could be provided in a form of, for example, a solid, a liquid or an emulsion, by any suitable method.

The present invention also provides a method for anti-fatigue, comprising administering to a subject in need an effective amount of a composition, wherein the composition comprises a first component being a *Cistanche tubulosa* extract and a second component being ubiquinone (Q10) and/or ubiquinol (QH). The applied type, applied route, applied form, applied frequency and related uses of the composition are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

[Preparation Examples]: Preparation of *Cistanche tubulosa* Extract 10 kg succulent stem of *Cistanche tubulosa* was cut into slices and soaked in water (*Cistanche tubulosa*:water=1:8 in volume) for 1 hour, stewed for 2 hours, and then filtered to collect a filtrate. The filtered residue was mixed with water (filtered residue:water=1:6 in volume) to provide a mixture, the mixture was stewed for 1 hour and then filtered to collect a filtrate; and the left residue was treated with the aforementioned operations to provide another filtrate. The three filtrates thus obtained were combined together, and then concentrated under vacuum at 50° C. to provide a concentrate with a specific gravity of 1.10. Thereafter, ethanol was added into the concentrate to a concentration of 60%, and the mixture thus obtained was refrigerated for 12 hours. The supernatant of the mixture was poured out and collected, and then the supernatant was concentrated under vacuum at 50° C. to provide 6 kg of crude extract with a specific gravity of 1.10, and the ethanol was recovered. Then, the crude extract was dissolved in hot water (crude extract:hot water=1:1 in volume) to provide a mixture. The mixture was injected into a macro-pore absorption resin column and sequentially eluted with 4 column volumes of water and 5 column volumes of 40% ethanol. Thereafter, the ethanol eluent was collected, and the water eluent was injected in the macro-pore absorption resin column and eluted with 3 column volumes of water, and then removed the water eluent. Thereafter, the column was eluted with 4 column volumes of 40% ethanol. The ethanol eluent was collected. The two ethanol eluents were concentrated and dried to provide about 1.1 kg of a dry matter (i.e., *Cistanche tubulosa* extract).

Example 1: Cellular Experiments

(1-1) Treatment of Cells

It is known that severe exercise or long-term exercise may lead to a large release of tumor necrosis factor alpha (TNF-α) and a decrease in mitochondria functions such as oxygen consumption rate (OCR, which represents the ability of aerobic metabolism of mitochondria) and extracellular acidification rate (ECAR, which represents the ability of glycolysis of mitochondria), so that the mitochondria cannot generate enough energy to supply cells in a subject, thereby resulting in the occurrence of fatigue in the subject. In this example, the C2C12 muscle cells with TNF-α induced damages were administered with the composition of the present invention, which comprises *Cistanche tubulosa* extract and ubiquinol, to understand the effect of the composition on anti-fatigue.

First, C2C12 cells (i.e., the muscle cells of mice; purchased from ATCC) were cultivated in an H-DMEM medium (purchased from Sigma company) containing 10% fetal bovine serum (purchased from BI company). After the C2C12 cells grew to the confluence rate of 80% (i.e., the mixed monolayer cells were accounted for 80% of the area), the cells were divided into seventeen groups (including a control group, a TNF-α group and fifteen experimental groups) and separately subjected to the following treatments:

1. Control group: cells were cultivated in an H-DMEM medium for 6 hours; and then, the medium was replaced with a differentiation medium (containing an H-DMEM medium and 2% horse serum), and the cells were continuously cultivated for another 4 days.
2. TNF-α group: cells were cultivated in an H-DMEM medium for 6 hours; and then, the medium was replaced with a differentiation medium (containing an H-DMEM medium and 2% horse serum) being externally added with TNF-α (to a final concentration of 10 ng/ml), and the cells were continuously cultivated overnight; finally, the medium was replaced with a differentiation medium, and the cells were cultivated for another 4 days.
3. Experimental groups 1 to 15: cells of each group were cultivated in an H-DMEM medium being externally added with 0.4 μl composition as shown in Table 1 for 6 hours; and then, the medium was replaced with a differentiation medium (containing an H-DMEM medium and 2% horse serum) being externally added with 0.4 μl composition as shown in Table 1 and TNF-α (to a final concentration of 10 ng/ml), and the cells were continuously cultivated overnight; finally, the medium was replaced with a differentiation medium being externally added with 0.4 μl composition as shown in Table 1, and the cells were cultivated for another 4 days. In Table 1, the extract and ubiquinol were dissolved in a differentiation medium, and the unit "μg/ml" represents the weight of extract (as dry weight) and/or ubiquinol (as dry weight) in every milliliter of the differentiation medium.

TABLE 1

| Experimental groups | Dry matter provided by [Preparation Examples] (i.e., *Cistanche tubulosa* extract) (μg/ml) | Ubiquinol (QH; purchased from Kaneka company) (μg/ml) | Weight ratio of extract:ubiquinol |
| --- | --- | --- | --- |
| 1 | 50 | 300 | 0.17:1 |
| 2 | 50 | 150 | 0.33:1 |
| 3 | 50 | 75 | 0.67:1 |
| 4 | 30 | 30 | 1:1 |
| 5 | 50 | 30 | 1.67:1 |
| 6 | 100 | 30 | 3.33:1 |
| 7 | 200 | 30 | 6.67:1 |
| 8 | 300 | 30 | 10:1 |
| 9 | 0 | 30 | — |
| 10 | 0 | 75 | — |
| 11 | 0 | 150 | — |
| 12 | 0 | 300 | — |
| 13 | 50 | 0 | — |
| 14 | 100 | 0 | — |
| 15 | 200 | 0 | — |

(1-2) Effect of the Composition Comprising *Cistanche tubulosa* Extract and Ubiquinol on Oxygen Consumption Rate The cells in the control group, TNF-α group and experimental groups 1 to 15 provided by Example (1-1) were respectively taken, and the oxygen consumption rates (including the oxygen consumption of ATP production and the oxygen consumption of maximal respiration) thereof were examined by a cell energy metabolism analyzer (Seahorse XF24). Then, the result of the control group was served as a basis (i.e., the oxygen consumption rate of the control group was set as 1-fold) to calculate the oxygen consumption rate of each group. The results are shown in FIGS. 1A and 1B.

Figure 1A:
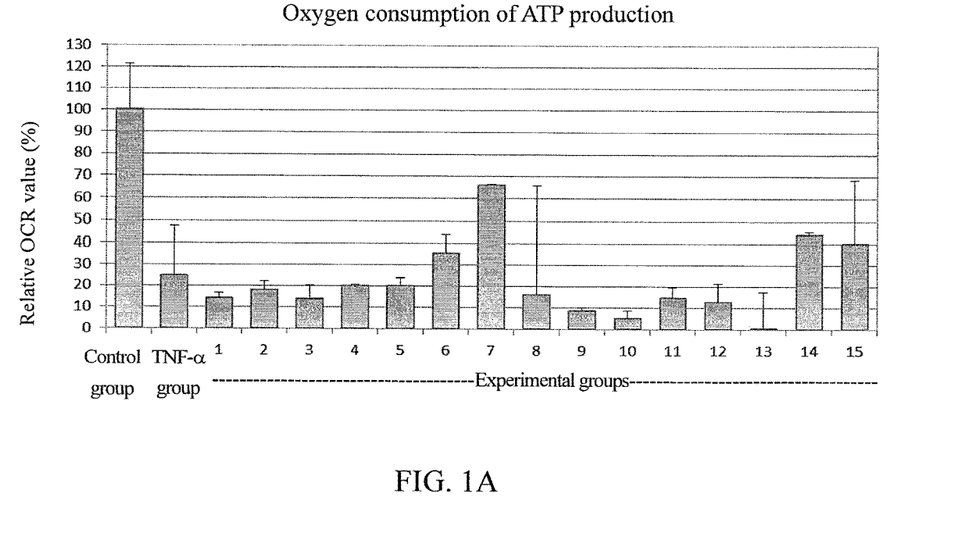
FIGS. 1A and 1B respectively show the oxygen consumption of ATP production and the oxygen consumption of maximal respiration of mitochondria in muscle cells, both including the results of the "Control group", "TNF-α group", and "Experimental groups 1 to 15", wherein the "Control group" was cultivated in a medium free of TNF-α, *Cistanche tubulosa* extract and ubiquinol; "TNF-α group" was cultivated in a medium being externally added with TNF-α but free of *Cistanche tubulosa* extract and ubiquinol; and "experimental groups 1 to 15" were cultivated in media being externally added with TNF-α, *Cistanche tubulosa* extract and/or ubiquinol.
Figure 1B:
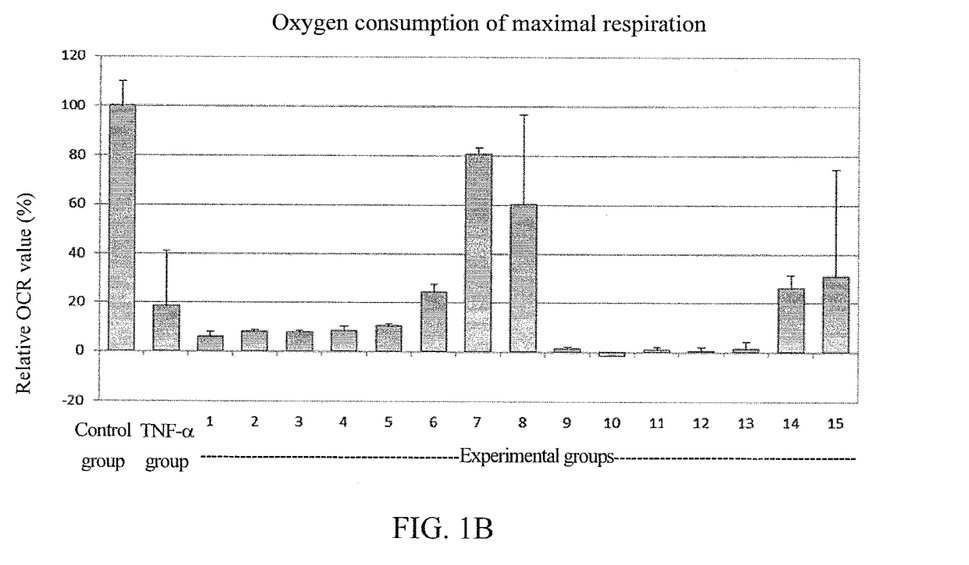

As shown in FIGS. 1A and 1B, as compared to the control group, the oxygen consumption of ATP production and the oxygen consumption of maximal respiration of cells in the TNF-α group all significantly decreased. These results indicate that TNF-α was indeed effective in inhibiting the respiration abilities of mitochondria, and thus the TNF-α induction can be used for imitating the condition of fatigue. As shown by the results of experimental groups 9 to 12, administering with ubiquinol alone cannot alleviate the TNF-α induced decreases in oxygen consumption of ATP production and oxygen consumption of maximal respiration. As shown by the results of experimental groups 1 to 8, administering the combination of *Cistanche tubulosa* extract and ubiquinol can effectively alleviate the TNF-α induced decreases in oxygen consumption of ATP production and oxygen consumption of maximal respiration, and the combinations of *Cistanche tubulosa* extract and ubiquinol at a weight ratio ranging from 0.67:1 to 10:1 (extract:ubiquinol) (i.e., experimental groups 3 to 8) have better effect.

The aforementioned results indicate that the composition of the present invention comprising a first component being a *Cistanche tubulosa* extract and a second component being ubiquinone (Q10) and/or ubiquinol (QH), particularly a composition comprising the aforementioned first component and second component at a weight ratio ranging from 0.67:1 to 10:1, can indeed effectively alleviate the TNF-α induced decrease in oxygen consumption rate, and thus, is effective in anti-fatigue.

(1-3) Effect of the Composition Comprising *Cistanche tubulosa* Extract and Ubiquinol on Extracellular Acidification Rate The extracellular acidification rate (including the glycolysis level and the glycolytic reserve) of the cells in the control group, TNF-α group and experimental groups 1 to 8 provided by Example (1-1) was examined by a cell energy metabolism analyzer. Then, the result of the control group was served as a basis (i.e., the extracellular acidification rate of the control group was set as 1-fold) to calculate the extracellular acidification rate of each group. The results are shown in FIGS. 2A and 2B.

Figure 2A:
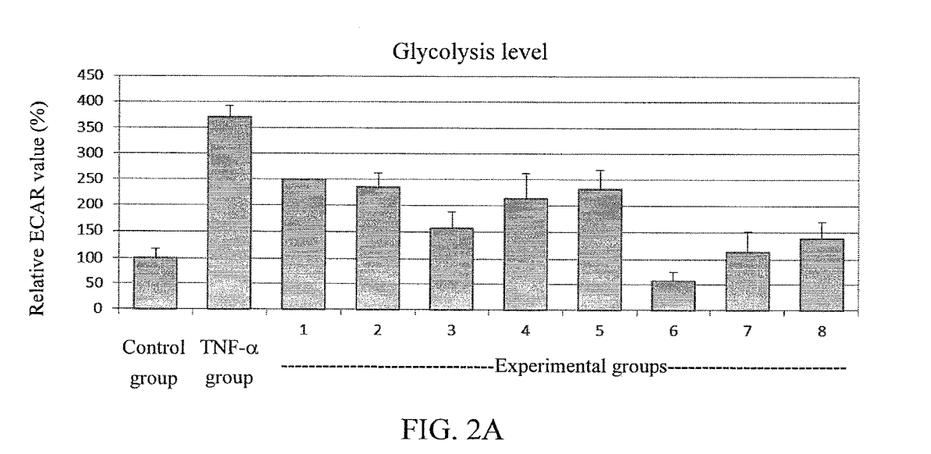
FIGS. 2A and 2B respectively show the glycolysis level and the glycolytic reserve of muscle cells, both including the results of the above "Control group", "TNF-α group", and "Experimental groups 1 to 15".
Figure 2B:
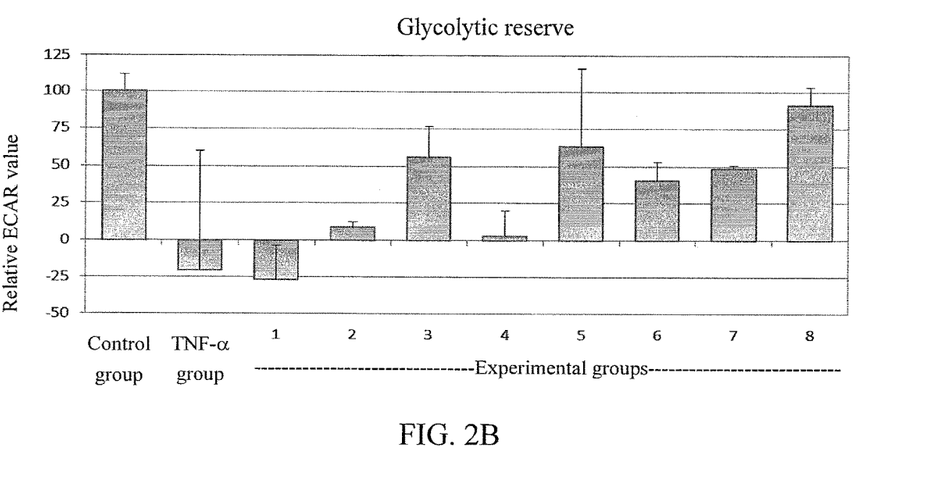

As shown in FIGS. 2A and 2B, as compared to the control group, the glycolysis level of TNF-α group significantly increased, and the glycolytic reserve of TNF-α group significantly decreased. These results indicate that TNF-α was indeed effective in increasing the glycolysis level and decreasing the glycolytic reserve of cells, and thus the TNF-α induction can be used for imitating the condition of fatigue. As shown by the results of experimental groups 1 to 8, administering the combination of *Cistanche tubulosa* extract and ubiquinol can effectively alleviate the TNF-α induced increase in glycolysis level and the TNF-α induced decrease in glycolytic reserve, and the combinations of *Cistanche tubulosa* extract and ubiquinol at a weight ratio ranging from 0.67:1 to 10:1 (extract:ubiquinol) (i.e., experimental groups 3 to 8) have better effect.

The aforementioned results indicate that the composition of the present invention comprising a first component being a *Cistanche tubulosa* extract and a second component being ubiquinone (Q10) and/or ubiquinol (QH), particularly a composition comprising the aforementioned first component and second component at a weight ratio ranging from 0.67:1 to 10:1, indeed can effectively alleviate the TNF-α induced abnormal in extracellular acidification rate, and thus, is effective in anti-fatigue.

Example 2: Animal Experiments

The fatigue indicators such as endurance, muscle strength and serum biochemical values (including serum lactate, serum ammonia, serum free fatty acid, serum glucose, serum creatine kinase (CK) activity) were evaluated by a mouse model in this example. It is known that serum lactate, serum ammonia and serum creatine kinase (CK) activity all are the metabolites produced after exercise, and thus an increase in these biochemical values represents an increased level of fatigue in mice. Furthermore, serum free fatty acid and serum glucose represent the glycolytic reserve of mice, and thus an increase in these biochemical values represents a decreased level of fatigue in mice.

(2-1) Establishment of Animal Models 8-week-old male ICR mice (purchased from BioLASCO company; average weight: about 25 to 30 g) were divided into four groups (6 mice in each group). The mice were fed for 14 days in a 12-hour day/12-hour night cycle (the diet was not limited, but each group were respectively fed with the compositions shown in Table 2 once a day by tube feeding).

TABLE 2

| Content of the ingredients in the composition | Group | | | |
|---|---|---|---|---|
| | Vehicle group | Group I | Group II | Group III |
| Wheat germ oil (ml) | 0.4 | 0.4 | 0.4 | 0.4 |
| Dry matter provided by [Preparation Examples] (i.e., *Cistanche tubulosa* extract (mg, as dry weight)) | 0 | 50.0 | 100.0 | 200.0 |
| Ubiquinol (mg, as dry weight) | 0 | 30.0 | 30.0 | 30.0 |
| Vitamin B1 (mg, as dry weight) | 0 | 10.0 | 10.0 | 10.0 |
| Vitamin E (mg, as dry weight) | 0 | 10.0 | 10.0 | 10.0 |
| Ribose (mg, as dry weight) | 0 | 50.0 | 50.0 | 50.0 |

In the fed compositions of the above Group I to Group III, the weight ratios of extract to ubiquinol (extract:ubiquinol) are shown in Table 3.

TABLE 3

| | Vehicle group | Group I | Group II | Group III |
|---|---|---|---|---|
| Weight ratio of extract:ubiquinol | — | 1.67:1 | 3.33:1 | 6.67:1 |

(2-2) Effect of the Composition Comprising *Cistanche tubulosa* Extract and Ubiquinol on Endurance Performance of Mice The mouse model of each group established by Example (2-1) was fastened with a plumbum wire (about 5% of its body weight) on back, and then, was forced to a weight-bearing swimming in a glass tank with water at 27° C. The length of time from starting swimming to submerging head under the water for at least 8 seconds (i.e., the time to exhaustion) were recorded. The results are shown in FIG. 3.

Figure 3:
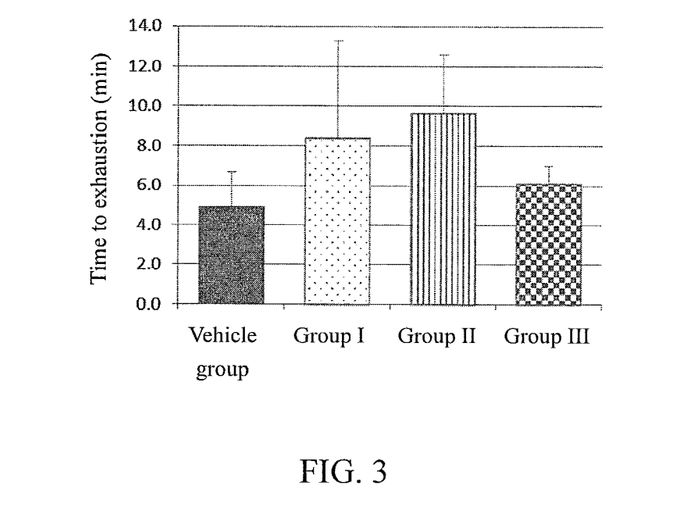

As shown in FIG. 3, as compared to the vehicle group, the times to exhaustion of mice in Groups I to III significantly increased, wherein time to exhaustion of mice in Group II increased most significantly. The results indicate that the composition of the present invention comprising a first component being a *Cistanche tubulosa* extract and a second component being ubiquinone (Q10) and/or ubiquinol (QH) can indeed increase endurance performance, increase athletic ability, and increase physical strength.

(2-3) Effect of the Composition Comprising *Cistanche tubulosa* Extract and Ubiquinol on Muscle Strength Performance of Mice The mouse model of each group established by Example (2-1) was subjected to a forelimb grip strength test by using a grip strength tester (purchased from Engineering, Nagoya, Japan) to understand the effect of the composition of the present invention on the muscle strength performance. The results are shown in FIG. 4.

Figure 4:
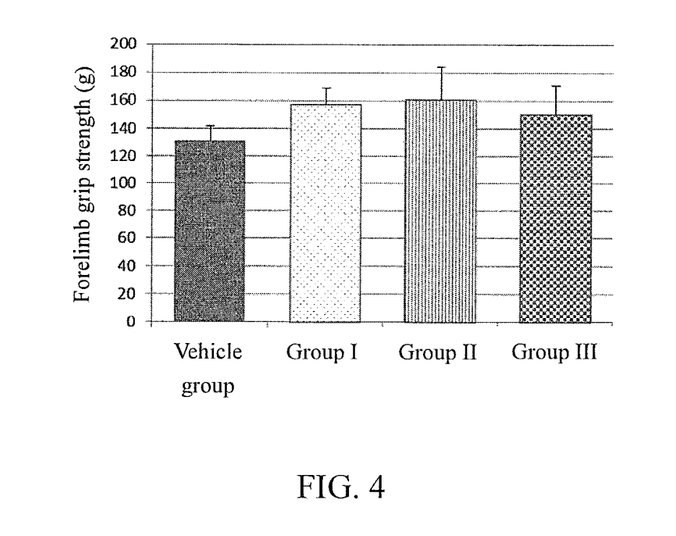
FIG. 4 shows the forelimb grip strength of mice after weight-bearing swimming, including the results of the above "Vehicle group", "Group I", "Group II" and "Group III".

As shown in FIG. 4, as compared to the vehicle group, the forelimb grip strength of mice of Groups I to III significantly increased. The results indicate that the composition of the present invention comprising a first component being a *Cistanche tubulosa* extract and a second component being ubiquinone (Q10) and/or ubiquinol (QH) can indeed increase muscle strength performance, increase athletic ability, and increase physical strength.

(2-4) Effect of the Composition Comprising *Cistanche tubulosa* Extract and Ubiquinol on Serum Biochemical Values of Mice The mouse model of each group established by Example (2-1) was subjected to swim exercise for 15 minutes. Then, the blood of each mouse was collected from orbital cavity for the following experiments.

(2-4-1) Changes of Serum Lactate Values

In this example, the serum lactate values of mice were detected by using the principles of enzymatic reaction and colorimetry. First, lactate oxidase was added into to the blood of mice of each group provided by Example (2-4) to react, and then 4-aminoantipyrine and 1,7-dihydroxynaphthalene were added into the blood to provide a liquid sample. After a red compound was produced in the liquid sample by the oxidase reaction, the absorbance value of the liquid sample was measured at the wavelength of 540 nm, and then, the absorbance was converted into the concentration of serum lactate. The results are shown in FIG. 5A.

Figure 5A:
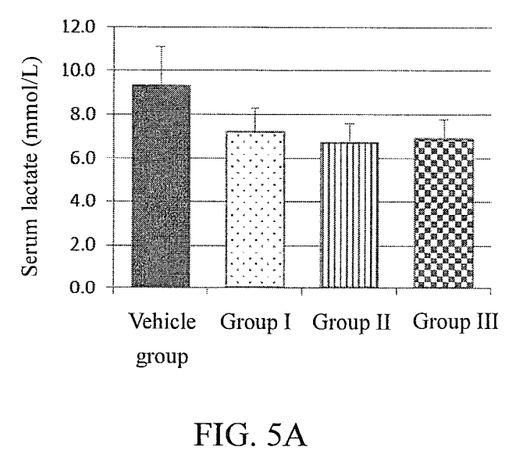
FIG. 5A shows the result of serum lactate.

As shown in FIG. 5A, as compared to the vehicle group, the serum lactate values of mice in Groups I to III all significantly decreased. The results indicate that the composition of the present invention comprising a first component being a *Cistanche tubulosa* extract and a second component being ubiquinone (Q10) and/or ubiquinol (QH) can indeed reduce the metabolites in the blood of mice after exercise, and thus, is effective in decreasing the level of fatigue in mice and is helpful for recovering physical strength and promoting fatigue elimination.

(2-4-2) Changes of Serum Ammonia Values

In this example, the serum ammonia values of mice were detected by using the principle of colorimetry. First, bromophenol blue as a coloring agent was added into the blood of mice in each group provided by Example (2-4) to provide a liquid sample. After a blue compound was produced in the liquid sample, the absorbance value of the liquid sample was measured at the wavelength of 605 nm, and then the absorbance was converted into the concentration of serum ammonia. The results are shown in FIG. 5B.

Figure 5B:
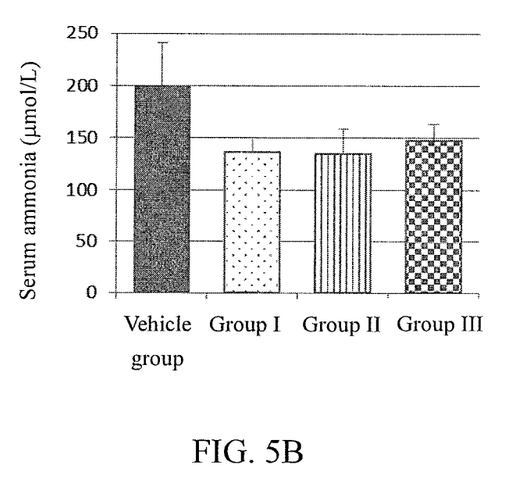
FIG. 5B shows the result of serum ammonia.

As shown in FIG. 5B, as compared to the vehicle group, the serum ammonia values of mice in Groups I to III all significantly decreased. The results indicate that the composition of the present invention comprising a first component being a *Cistanche tubulosa* extract and a second component being ubiquinone (Q10) and/or ubiquinol (QH) can indeed reduce the metabolites in the blood of mice after exercise, and thus, is effective in decreasing the level of fatigue in mice and is helpful for recovering physical strength and promoting fatigue elimination.

(2-4-3) Changes of Serum Free Fatty Acid Values

In this example, the serum free fatty acid values of mice were detected by using the principles of enzymatic reaction and colorimetry. First, acyl CoA synthetase, acyl CoA oxidase and peroxidase were added into the blood of mice in each group provided by Example (2-4) to provide a liquid sample. After a purple compound was produced in the liquid sample by the reaction, the absorbance value of the liquid sample was measured at the wavelength of 550 nm, and then the absorbance was converted into the concentration of serum free fatty acid. The results are shown in FIG. 5C.

Figure 5C:
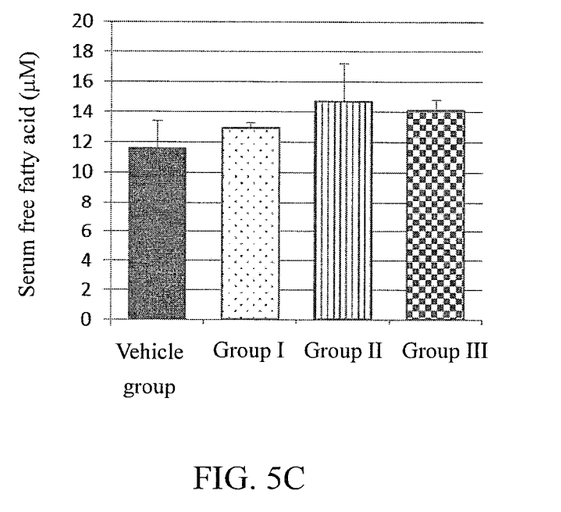
FIG. 5C shows the result of serum free fatty acid.

As shown in FIG. 5C, as compared to the vehicle group, the serum free fatty acid values of mice in Groups II and III both significantly increased. The results indicate that the composition of the present invention comprising a first component being a *Cistanche tubulosa* extract and a second component being ubiquinone (Q10) and/or ubiquinol (QH) can indeed increase the reserved energy in the blood of mice, and thus, is effective in decreasing the level of fatigue in mice and is helpful for recovering physical strength and promoting fatigue elimination.

(2-4-4) Changes of Serum Glucose Values

In this example, the serum glucose values of mice were detected by using the principles of enzymatic reaction and colorimetry. First, glucose oxidase was added into the blood of mice in each group provided by Example (2-4) to react, and then 4-aminoantipyrine and 1,7-dihydroxynaphthalene were added into the blood to provide a liquid sample. After a red compound was produced in the liquid sample by the oxidase reaction, the absorbance value of the liquid sample was measured at the wavelength of 555 nm, and then the absorbance was converted into the concentration of serum glucose. The results are shown in FIG. 5D.

Figure 5D:
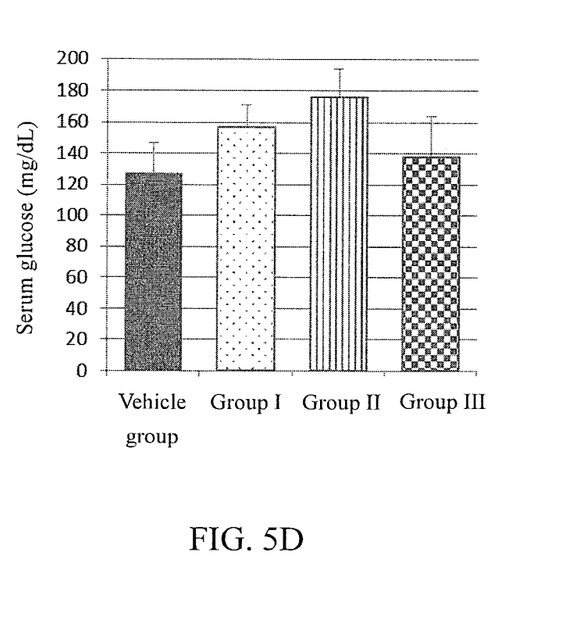
FIG. 5D shows the result of serum glucose.

As shown in FIG. 5D, as compared to the vehicle group, the serum glucose values in mice of Groups I and II both significantly increased. The results indicate that the composition of the present invention comprising a first component being a *Cistanche tubulosa* extract and a second component being ubiquinone (Q10) and/or ubiquinol (QH) can indeed increase the reserved energy in the blood of mice, and thus, is effective in decreasing the level of fatigue in mice and is helpful for recovering physical strength and promoting fatigue elimination.

(2-4-5) Changes of Serum Creatine Kinase Values

In this example, the serum creatine kinase values were detected by using the principles of enzymatic reaction and colorimetry. First, creatine phosphate glucose oxidase was added into the blood of mice in each group provided by Example (2-4) to react, and then 4-aminoantipyrine and 1,7-dihydroxynaphthalene were added into the blood to provide a liquid sample. After a white compound was produced in the liquid sample by the oxidase reaction, the absorbance value of the liquid sample was measured at the wavelength of 680 nm, and then the absorbance was converted into the concentration of serum creatine kinase. The results are shown in FIG. 5E.

Figure 5E:
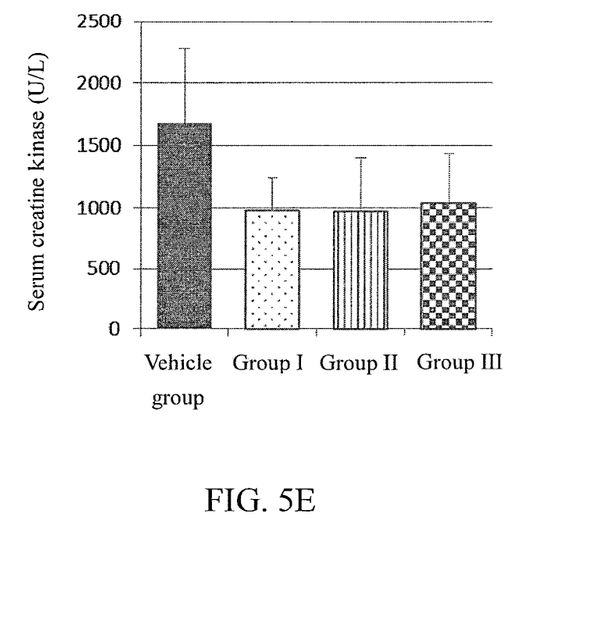
FIG. 5E shows the result of serum creatine kinase (CK) activity.

As shown in FIG. 5E, as compared to the vehicle group, the serum glucose values of mice in Groups I to III all significantly decreased. The results indicate that the composition of the present invention comprising a first component being a *Cistanche tubulosa* extract and a second component being ubiquinone (Q10) and/or ubiquinol (QH) can indeed reduce the metabolites in the blood of mice after exercise, and thus, is effective in decreasing the level of fatigue in mice and is helpful for recovering physical strength and promoting fatigue elimination.

As shown by the above experimental results, the composition of the present invention comprising a first component being a *Cistanche tubulosa* extract and a second component being ubiquinone (Q10) and/or ubiquinol (QH), particularly a composition comprising the aforementioned first component and second component at a weight ratio ranging from 0.67:1 to 10:1, can effectively alleviate the TNF-α induced decreases in oxygen consumption of ATP production and oxygen consumption of maximal respiration, and can alleviate the TNF-α induced increase in glycolysis level of cells, thereby increasing the glycolytic reserve of cells. In addition, the composition of the present invention can increase endurance and muscle strength of mice, reduce the metabolites in the blood of mice after exercise, and increase the reserved energy in the blood of mice after exercise. Therefore, the composition of the present invention is effective in anti-fatigue and can be used for at least one of treating chronic fatigue syndrome, preventing chronic fatigue syndrome, increase endurance performance, increase athletic ability, increase physical strength, recovering physical strength, promoting fatigue elimination, preventing myocardial weakness, helping ameliorate myocardial weakness and helping improve cardiac function.

What is claimed is:

1. A method for anti-fatigue, comprising administering to a subject in need an effective amount of a composition, wherein the composition comprises a first component being a *Cistanche tubulosa* extract and a second component being ubiquinone (Q10) and/or ubiquinol (QH), and the weight ratio of the first component to the second component ranges from 1.67:1 to 10:1.

2. The method as claimed in claim 1, wherein the composition is administered to the subject by oral administration, transdermal administration, intravenous injection and/or subcutaneous injection.

3. The method as claimed in claim 2, wherein the composition is administered to the subject by oral administration, thereby achieving at least one of treating chronic fatigue syndrome, preventing chronic fatigue syndrome, increasing endurance performance, increasing athletic ability, increasing physical strength, recovering physical strength, eliminating fatigue, preventing myocardial weakness, helping ameliorate cardiac weakness, and helping improve cardiac function.

4. The method as claimed in claim 2, wherein the composition is administered to the subject by transdermal administration, thereby treating chronic fatigue syndrome and/or preventing chronic fatigue syndrome.

5. The method as claimed in claim 2, wherein the composition is administered to the subject by intravenous injection, thereby treating chronic fatigue syndrome and/or preventing chronic fatigue syndrome.

6. The method as claimed in claim 2, wherein the composition is administered to the subject by subcutaneous injection, thereby treating chronic fatigue syndrome and/or preventing chronic fatigue syndrome.

* * * * *